(12) United States Patent
Mann et al.

(10) Patent No.: US 6,609,029 B1
(45) Date of Patent: Aug. 19, 2003

(54) CLIP LOCK MECHANISM FOR RETAINING LEAD

(75) Inventors: Carla M. Mann, Los Angeles, CA (US); Larry D. Devor, Menifee, CA (US); Stephen L. Goldman, Stevenson Ranch, CA (US); Donald L. Sandford, Northridge, CA (US); Grace Ying Yang Jang, Calabasas, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 170 days.

(21) Appl. No.: 09/750,634

(22) Filed: Dec. 28, 2000

Related U.S. Application Data

(60) Provisional application No. 60/180,433, filed on Feb. 4, 2000.

(51) Int. Cl.[7] ............................................. A61N 1/375
(52) U.S. Cl. ......................................................... 607/37
(58) Field of Search ................................. 439/278, 282, 439/296, 345, 595, 660, 668, 669, 670, 909; 607/36, 37

(56) References Cited

U.S. PATENT DOCUMENTS

| | | | |
|---|---|---|---|
| 4,310,001 A | * 1/1982 | Comben | 128/419 P |
| 4,461,194 A | 7/1984 | Moore | 81/436 |
| 4,614,395 A | 9/1986 | Peers-Trevarton | 339/97 |
| 4,860,750 A | 8/1989 | Frey et al. | 128/419 |
| 5,086,773 A | 2/1992 | Ware | 128/419 |
| 5,252,090 A | 10/1993 | Giurtino et al. | 439/441 |
| 5,261,395 A | * 11/1993 | Oleen et al. | 607/15 |
| 5,324,312 A | 6/1994 | Stokes et al. | 607/37 |
| 5,368,496 A | 11/1994 | Ranalletta et al. | 439/261 |
| 5,433,734 A | 7/1995 | Stokes et al. | 607/37 |
| 5,560,358 A | 10/1996 | Arnold et al. | 128/642 |
| 5,766,042 A | 6/1998 | Ries et al. | 439/668 |
| 5,906,634 A | 5/1999 | Flynn et al. | 607/37 |
| 5,951,595 A | 9/1999 | Moberg et al. | 607/37 |
| 6,198,969 B1 | 3/2001 | Kuzma | 607/37 |

* cited by examiner

*Primary Examiner*—Jeffrey R. Jastrzab
*Assistant Examiner*—Frances P. Oropeza
(74) *Attorney, Agent, or Firm*—Laura Haburay Bishop; Bryant R. Gold

(57) ABSTRACT

A straight-forward and tool-less mechanism is provided for securing lead wires to an implantable neurostimulator, or similar medical device. In one embodiment, a clip lock mechanism is pivotally connected to the enclosure of the medical device, which enclosure also includes at least one receptacle with contacts to the components within the device. The proximal end of the lead wires terminate in a connector, including at least one plug and at least one pin with contacts corresponding to the electrodes or other devices along the distal end of the lead. The pin is inserted into the receptacle, thus completing the connection between the pin and receptacle contacts, and the clip is pivoted over the plug. The plug preferably has depressions that provide a clear visual and tactual indication of the position of the properly placed clip.

21 Claims, 8 Drawing Sheets

CLIP LOCK MECHANISM FOR RETAINING LEAD

This application claims the benefit of U.S. Provisional Application Serial No. 60/180,433, filed Feb. 4, 2000, which application is incorporated herein by reference.

FIELD OF THE INVENTION

The present invention generally relates to a medical device for implantation in a living body, and more particularly relates to a clip lock mechanism for lead wires used with an implantable medical device.

BACKGROUND OF THE INVENTION

A variety of devices exist which make use of electrical lead wires, i.e., leads or lead extensions, that detachably connect to an electrical device. For instance, numerous medical devices, such as neural stimulation devices, cardiac pacemakers and defibrillators, commonly establish a connection between an implanted lead or lead extension (herein, both will be referred to as 'lead') and an implanted electronic package. In a typical pacemaker, the proximal end of a lead is connected to an implantable pulse generator, while the distal end, containing one or more electrodes, is typically inserted in or on the heart.

It is preferable that the leads be detachable from the devices so that either may be implanted, explanted or replaced without affecting the other. Detaching and attaching the lead to the device should be simple, to reduce surgical time, and evident, to limit chances for error. In addition, it is preferable that attachment and detachment be possible without a tool. While the lead is attached to the device, the connection should be strong enough to resist flexing and any other forces that could unintentionally disconnect the lead.

The connection between a lead and an implantable device is preferably compact and light-weight, and it must be constructed of biocompatible materials and in such a way so that the electronic circuitry can survive for extended periods of time without any significant changes in performance. In addition to the connection being mechanically reliable, so that a lead does not inadvertently become disconnected from the device, it must also ensure proper electrical communication between the device and lead(s) at all times.

It is known in the art to use a set screw for each connection, often providing electrical contact, as well as mechanical connection, between the lead(s) and the device. This arrangement requires delicate and time-consuming surgical procedures ensuring that the set screw is secure yet does not strip, and that the device is not damaged. In addition, this arrangement is rather bulky. Also, sealing set screws from the surrounding body fluids is often difficult, as the seal may be damaged during tightening of the set screw.

There exists a need in the art for a compact, easy to operate, fast, and reliable way to detachably secure leads to implantable electronic packages.

BRIEF SUMMARY OF THE INVENTION

The present invention addresses the above and other needs by providing a clip lock mechanism for securing lead wires, i.e., lead or lead extension, to an, implantable neurostimulator, or similar implantable device.

The clip lock mechanism of the present invention preferably applies to an enclosure made of a case and a header. However, the invention also may be used with one-piece devices, i.e. headerless enclosures, as well as with multi-piece enclosures. With the case and header enclosure, the case is made of a biocompatible material (e.g. titanium or ceramic) and houses an electronic circuit assembly (hereafter also referred to as "electronic circuitry", "circuitry", or "electronics").

The header, which is typically made of polymeric material, such as epoxy, is secured (e.g. molded in place) to the case. The header has a plurality of electrical connectors (electrical feed-through terminals) passing through it connecting to the electronic components inside the case. In addition, the header has a receptacle(s) where a lead connector(s) at the proximal end of a lead(s) or lead extension(s) is inserted to form the electro-mechanical connection between the electronics and leads.

The clip lock mechanism provided by the present invention is typically made of a medical grade metal such as 316 stainless steel or nitinol. The clip lock mechanism pivotally connects to the header. The lead connector (at the proximal end of a lead or lead extension) comprises at least one pin and a plug. Once the pin(s) of the connector have been inserted into the receptacle, the clip is pivoted over the lead plug. The plug preferably has depressions that provide a clear visual and tactual indication of the position of the properly placed clip. Advantageously, manipulation of the clip is straight-forward, simple, and tool-less, yet the clip is reliably locked in place and requires intentional manipulation to be unlatched.

BRIEF DESSCRIPTION OF THE DRAWINGS

The above and other aspects, features, and advantages of the present invention will be more apparent from the following more particular description thereof, presented in conjunction with the following drawings wherein.

Figure 8A:
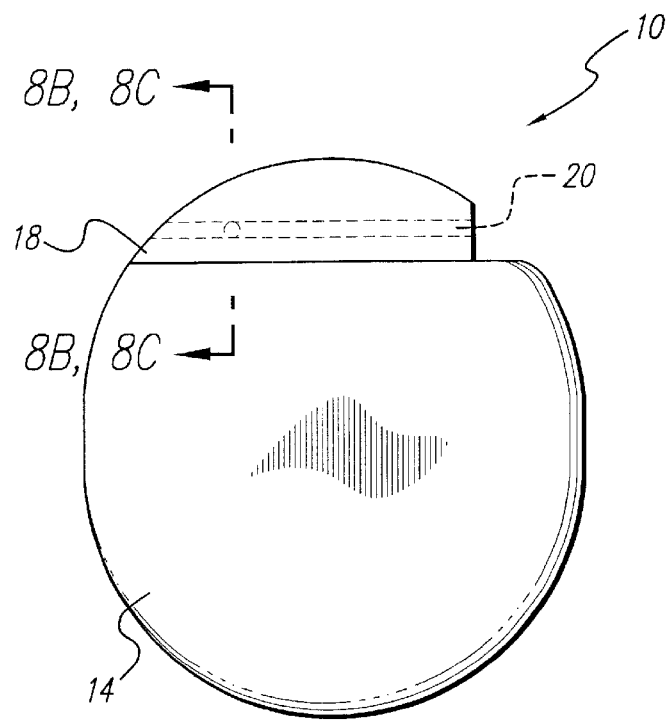
FIG. 8A is a front view of a spring-loaded pin of another embodiment of the present invention, and medical device of the type that may be used with the present invention.
Figure 8B:
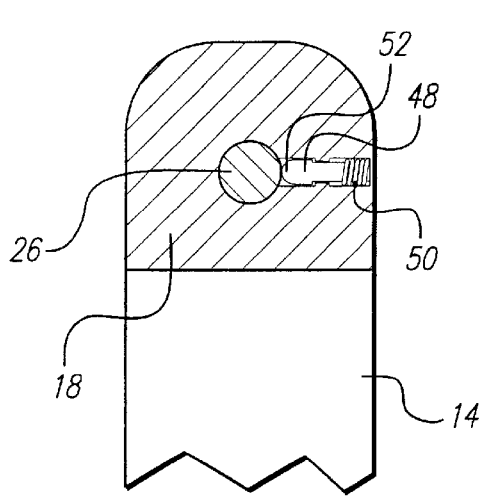
FIG. 8B is a side cross-sectional view of the spring-loaded pin taken along line 8B—8B of FIG. 8A of another embodiment of the present invention, with the spring of the spring-loaded pin in a compressed position, and medical device of the type that may be used with the present invention.
Figure 8C:
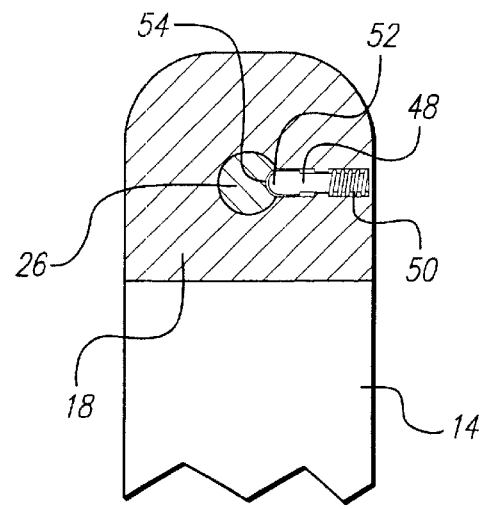
Figure 9:
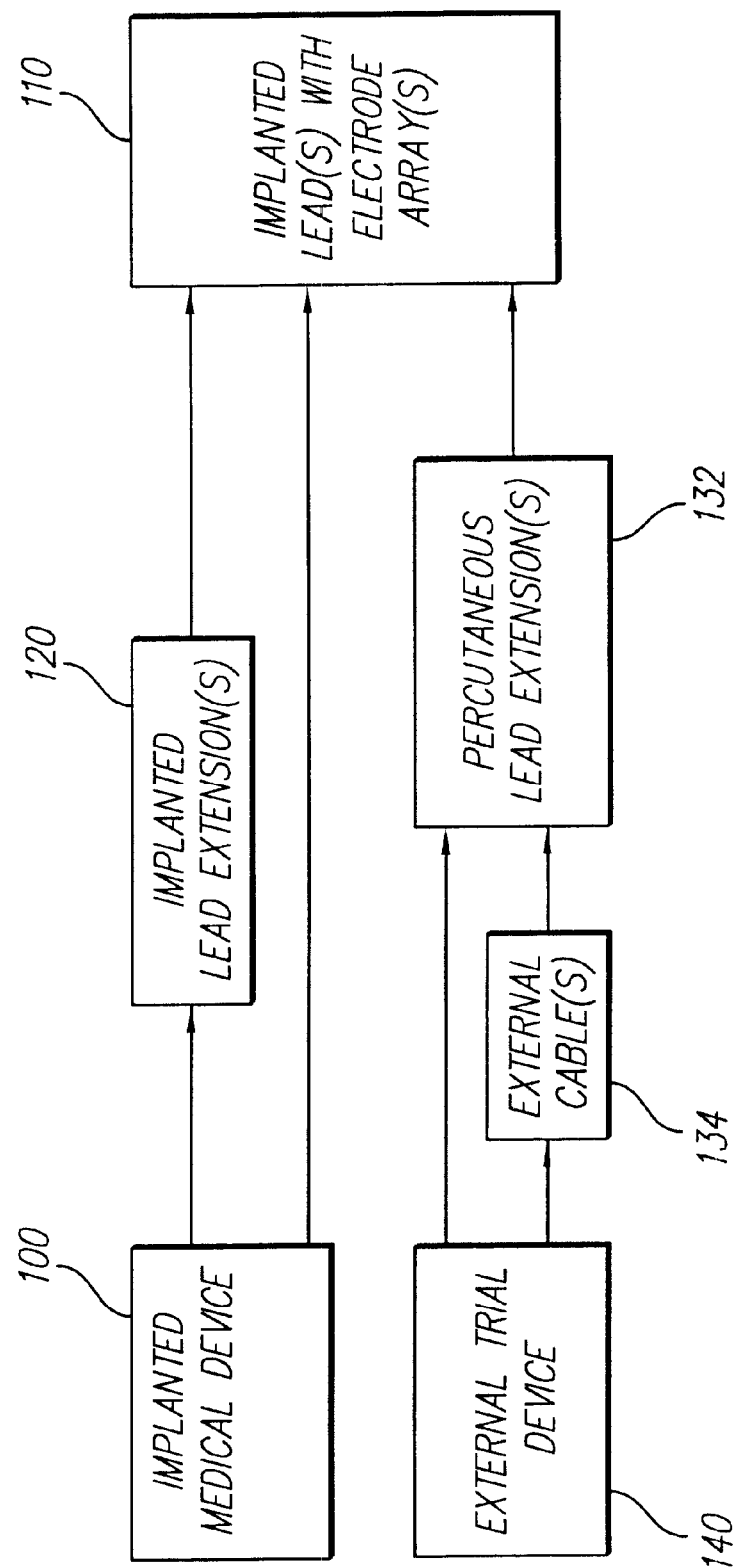

FIG. 8C is a side cross-sectional view of the spring-loaded pin taken along line 8C—8C of FIG. 8A of another embodiment of the present invention, with the spring of the spring-loaded pin in a relaxed position, and medical device of the type that may be used with the present invention; and FIG. 9 is a block diagram that illustrates the various connections between components of a typical medical device of the invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
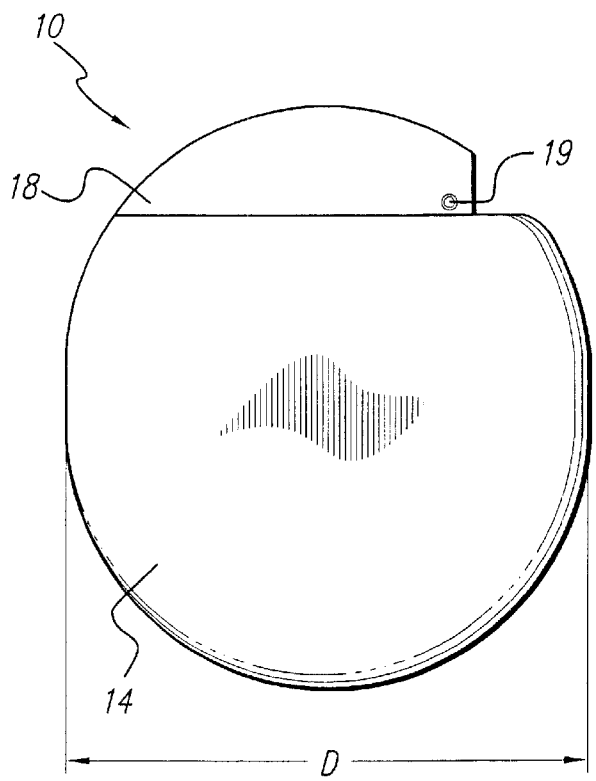
FIG. 1A is a front view of a medical device of the type that may be used with the present invention.

For illustration purposes, the following description of the present invention is shown in conjunction with an implantable electronic package or device 10, shown, e.g., in FIG. 1A. The implantable electronic device 10 typically comprises a sealed medical device that carries out a desired medical function, e.g., stimulation of the spinal cord or other nerves. The device 10 preferably comprises an enclosure made of a case 14 enclosing an electronic and/or mechanical assembly (not shown in FIG. 1A) and a header 18 for closing the package. However, the device may be a one-piece enclosure, i.e., headerless, or a multiple piece enclosure. The electronic or other components are configured in a desired circuit and/or mechanical relationship so that the device 10 is able to carry out its intended function, e.g., neurostimulation, sensing, monitoring, or the like.

Figure 1B:
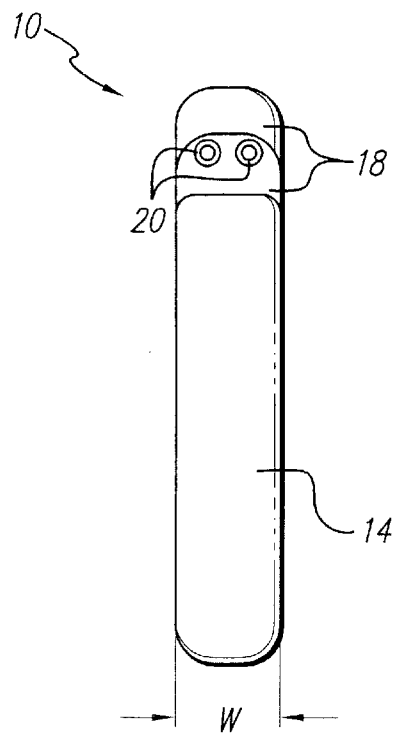
FIG. 1B is a side view of the medical device of FIG. 1A.

The case 14 is made of a biocompatible material, such as titanium. It should be understood, however, that the case 14 could be made from other suitable implantable materials, such as ceramic. As illustrated in FIGS. 1A and 1B, the case is preferably rounded, with smooth curved transitions that eliminate or minimize edges or sharp corners. The case preferably has a maximum circular diameter D of about 55 mm, and more preferably only about 45 mm (or dimensions encompassing a similar area) or less. The maximum thickness W of the case is preferably about 10 mm, and is more preferably only about 8 mm or less. However, case 14 may be formed to any desired shape and dimension by processes known to those skilled in the art of forming the chosen biocompatible material.

Figure 3A:
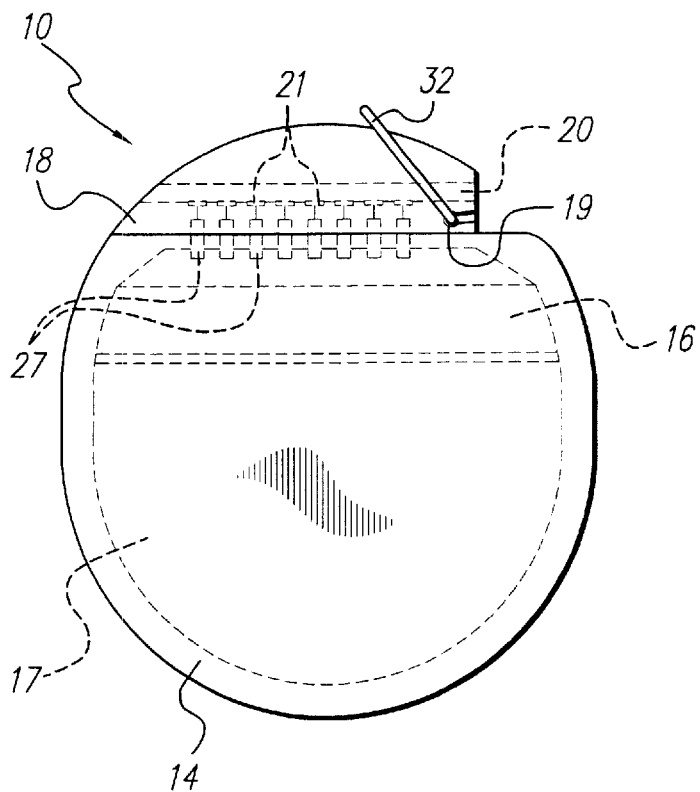
FIG. 3A is a front view of the medical device including the clip lock mechanism of one embodiment of the present invention.

The electronic assembly 16 shown in FIG. 3A includes a circuit board on or in which various individual components are mounted, formed, or otherwise carried. Components may include, e.g, a permanent magnet, an antenna coil, integrated circuit (IC) chip(s), capacitors, resistors, inductors, transistors, and the like. The circuit board is connected at one end to a plate which is configured to mate with the open edge of the case 14. A bond between the plate and case 14, typically made by laser welding or other known process, holds the assembly in place within case 14. Representative assembly techniques that may be used to hermetically seal an electronic package within a case are taught in U.S. Pat. No. 4,991,582, incorporated herein by reference.

Figure 2:
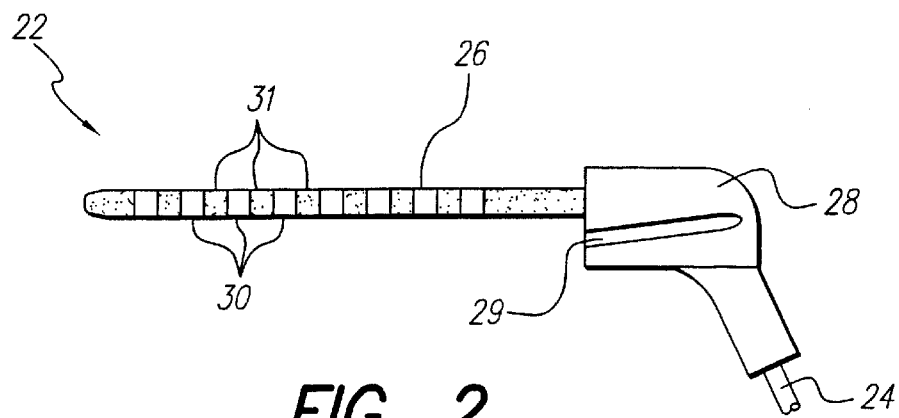
FIG. 2 is a front view of a lead connector, prior to insertion into the device of FIGS. 1A and 1B.

Header 18, when used, is made of biocompatible material, typically a polymeric material such as epoxy, polyurethane, or polysulfone. A plurality of electrical connectors (electrical feed-through terminals 27) pass through header 18, connecting to the electronic assembly 16 inside the case 14. A power source, e.g., a rechargeable battery 17, is also typically contained within case 14 and connected to assembly 16. Ultimately the components inside case 14 need to be connected to the electrode arrays or other devices at and/or along the distal end of a lead(s). The lead, i.e., lead system, typically comprises lead wires within a lead cable 24, lead blank(s) with electrode arrays or other devices at and/or along its distal end, and possibly lead extension(s). Thus, lead cable 24 may enclose lead wires in a lead or in a lead extension. At the proximal end of the lead cable 24 is a lead connector 22 (FIG. 2). Header 18 has receptacle(s) 20 where the lead connector 22 is inserted to form the electromechanical connection between the components inside case 14 and lead wires within lead cable 24.

As is known in the art, header 18 may be created by inserting case 14 including the electronic/mechanical assembly 16 and feed-through terminals 27 into a mold, wherein the material of header 18 is molded in place. A mold insert, also known in the art, is preferably used to retain a space for the lead receptacle(s) 20. Alternatively, the space for the receptacles 20 may be drilled out after molding of the header 18. As is known in the art, a suture hole(s) may be included at the top of the header, to assist in holding the device in a desired implanted location. This suture hole(s) may be formed in a similar manner as described above for the lead receptacle(s).

Turning now to FIG. 2, lead connector 22 connects a plurality of electrical lead wires in a lead cable 24 to the electronic or other components 16 inside of device 10 through the electrical feed-through pins or terminals 27 located in header 18. For instance, in the case of a neural stimulator, device 10 includes n feed-through terminals to allow electrical contact to be individually made from inside the hermetically-sealed device with the n electrodes that form part of the lead system. The n electrodes are typically assembled into an array at the distal end (not shown), and/or spaced apart along the length of the lead cable 24.

As indicated earlier, connector 22 is typically found at the proximal end of an implantable lead cable 24. Connector 22 typically includes at least one lead pin 26 and lead plug 28.

At the distal end (not shown) of the lead cable 24, or along the length of the lead cable 24, there will typically be an array of electrodes, or other components (e.g., a sensor) to which the components within device 10 must be electrically connected.

Each electrode or other component is connected to a suitable wire within the lead cable 24. Each wire that passes through lead cable 24 to an electrode or other electrical component is connected to a lead contact 30 of the lead connector 22 at the proximal end of the lead cable 24. Lead contacts 30 are typically made of, for instance, stainless steel, titanium, tantalum, or noble metal(s) such as platinum or platinum iridium. Separating lead contacts 30 are electrical insulators 31, typically made of polyurethane, silicone, epoxy, or polytetrafluoroethylene (PTFE). Lead contacts 30 are formed along the length of the lead pin 26 so as to make electrical contact with lead receptacle contacts 21 formed along the inside of receptacle 20 when the connector 22 is inserted in receptacle 20. Lead receptacle contacts are in turn in electrical contact with feed-through terminals 27, and thus with assembly 16.

For ease of handling, and in this case, also working in conjunction with the clip lock mechanism, a lead plug 28 is used at the transition from the lead cable 24 to the lead pin 26. The lead plug 28 is typically cast or molded of an elastomeric or rigid polymer material such as polyurethane or silicone. Other configurations of lead contacts, electrical insulators, and lead plugs within a lead connector, as are known in the art, may also be useful with the present invention. The process of making a connector such as lead connector 22 is known to those of skill in the art.

It is the function of the connector 22 to electrically connect the lead wires within the lead cable 24 (and hence to electrically connect the electrodes or other components at the distal end or along the length of the lead cable 24) to the feed-through terminals 27 through the lead receptacle contacts 21 which are located in header 18. That is, it is the function of the connector 22 to ultimately connect the distal electrodes/sensor(s) to the assembly 16 housed within the device 10, thereby allowing the device 10 to perform its intended function. Thus, each wire within the lead cable 24 is electrically connected to a corresponding contact point 30 placed along the length of lead pin 26. The metal contacts 30 in the connector 22 are positioned so as to match or "align" with corresponding lead receptacle contacts 21, and are thus in electrical contact with feed-through terminals 27 of the header 18 when the connector 22 is placed in the receptacle 20. Lead contacts 30 of lead connector 22 are configured to be flush with the inside surface of lead receptacle 20. Thus, when lead connector 22 is fully inserted into lead receptacle 20, with lead plug 28 being flush against header 18, each lead contact 30 along the lead pin 26 aligns with and electrically contacts a respective conductive lead receptacle contact 21 of header 18.

Figure 3B:
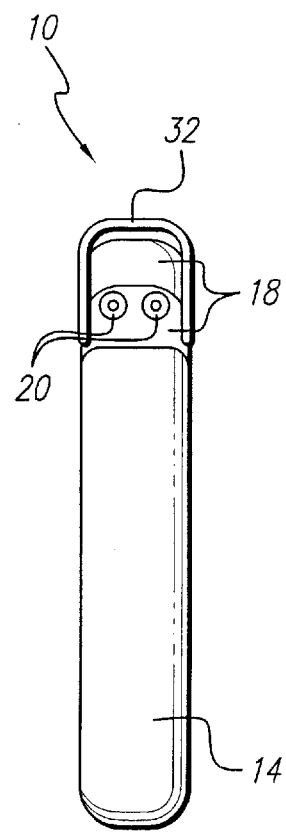
FIG. 3B is a side view of the medical device including the clip lock mechanism of one embodiment of the present invention.

Turning again to FIGS. 3A and 3B, the clip lock mechanism 32 of the present invention is shown. Clip 32 is preferably made of a durable, biocompatible, medical grade material, more preferably of 316 stainless steel or similar metal or metal alloy, and most preferably of nitinol. The clip 32 comprises a wire, of approximately 1 mm or less diameter, or any suitable diameter, bent into the shape of a rectangle with rounded corners. The material properties and cross-sectional geometry of the wire should be such that the clip is strong enough to endure assembly, handling, and use, while being as unobtrusive as possible. To impart the necessary resilience to the clip, a steel wire is spring-tempered via standard means known to those of ordinary skill in the art of forming and treating steel, and similarly, a nitinol wire is formed and treated via standard means known to those of ordinary skill in that art. An advantage, inter alia, of the clip locking mechanism of the present invention is its simplicity and associated small size, low profile, tool-less activation, and lightweight design, especially as compared to the prior art mechanisms.

Figure 4A:
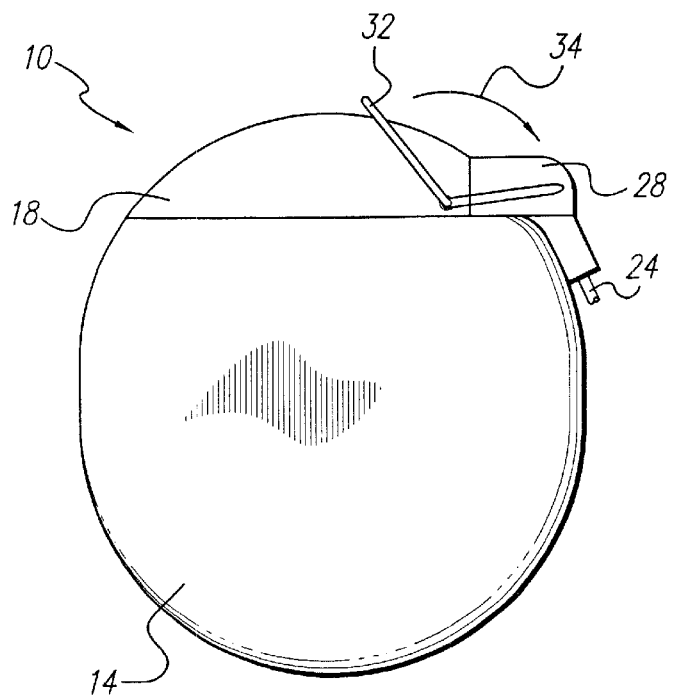
FIG. 4A is a front view of the lead connector of FIG. 2 installed into the device of FIGS. 3A and 3B, prior to locking the clip into place over the lead plug.
Figure 4B:
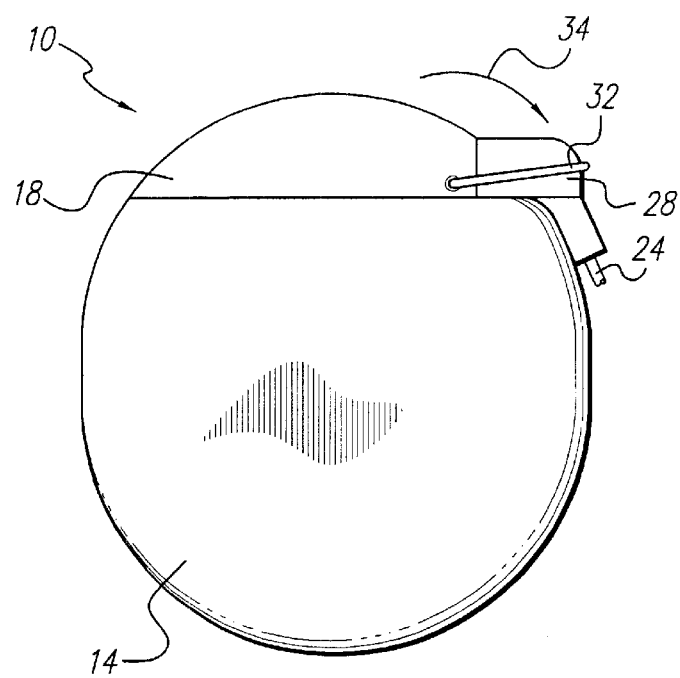
FIG. 4B is a front view of the lead connector of FIG. 2 installed into the device of FIGS. 3A and 3B, with the clip locked into place over the lead plug.

The minimum width of clip 32 along the shorter sides of the rectangle should be determined by the width of the lead plug 28. The minimum length of clip 32 along the longer sides of the rectangle should be determined by the length of the lead plug 28. The length and width of clip 32 should allow the clip to pivot over and secure the lead plug 28 to device 10, as shown in FIGS. 4A and 4B. Lead plug 28 preferably includes a groove 29 or indentations along its length, or more preferably, about its periphery, allowing clip 32 to snap or settle snugly into place around the plug 28, securing plug 28 to header 18.

Figure 3C:
FIG. 3C is a side view of the clip lock mechanism of one embodiment of the present invention.

As best seen in FIG. 3C, a break, or gap, along the generally rectangular clip 32 is used for securing the clip to the header 18 of the device 10 (or directly to the case of a headerless device). Assuming plug 28 is longer than it is wide, as in FIG. 2, the break or gap in clip 32 would be along one of the shorter sides of the generally rectangular clip shape, preferably at or near the midpoint of the side. A hole 19 or indentations in the header 18, preferably just slightly larger in diameter than the wire of the clip, allow the ends of the wire to be inserted into the hole or indentations. These holes 19 or indentations could be drilled after molding of header 18. Alternatively, the holes 19, indentations, and/or clip may be molded in place during molding of the header 18.

During insertion of lead connector 22 into receptacle 20, clip 32 is in an unlocked position, as shown in FIG. 4A. After the lead plug 28 is flush against header 18, clip 32 may simply be pivoted with a finger in the direction of arrow 34 into place over plug 28, as shown in FIG. 4B. Of course, the clip may be manipulated with a tool, if desired, but is configured in such a way that a tool is not necessary. As previously described, grooves 29 or indentations along plug 28 allow clip 32 to be firmly snapped into place and secured in position over the connector. The connector is thus locked into place, so that only intentional manipulation of the clip will disconnect the lead. Once the connector 22 is fully inserted into the receptacle 20 of header 18, both the lead pin 26 and the connections within the header are generally protected from body fluids via a seal provided by the receptacle and pin mating shapes and their materials (e.g., polyurethane, silicone, epoxy, PTFE).

If ever there is a need to remove, explant, or replace a lead, lead extension, or device 10, the lead cable 24 may be detached from the device 10 by simply pivoting the lead clip 32 in the direction opposite arrow 34, and then pulling connector 22 from the receptacle 20. The simple and sure mechanism of the present invention results in reduced surgical time and possible error, while ensuring a secure connection between the electrodes or other devices at or along the distal end of the lead(s) and the components within device 10.

Other clip shapes, sizes, and configurations will be apparent to those of skill in the art, such as a clip of generally oval or circular shape or a clip including a tab for ease of manipulation. Likewise, the clip may have a break in a position anywhere along its length, and be attached to the device in any appropriate way (e.g., the clip may extend through a hole in the device or the clip may be formed in place) as necessitated by the clip design. Alternatively, if the wire that forms the clip is welded together at its ends, the clip may not have a break anywhere along its length. In addition, rather than a pivoting wire, secured at all times through the device, a clip could be connected to the device at only one end. Once the connector was inserted, the wire clip could swing into place over the plug, and the free end of the wire inserted into a hole or indentation in the device.

Figure 5A:
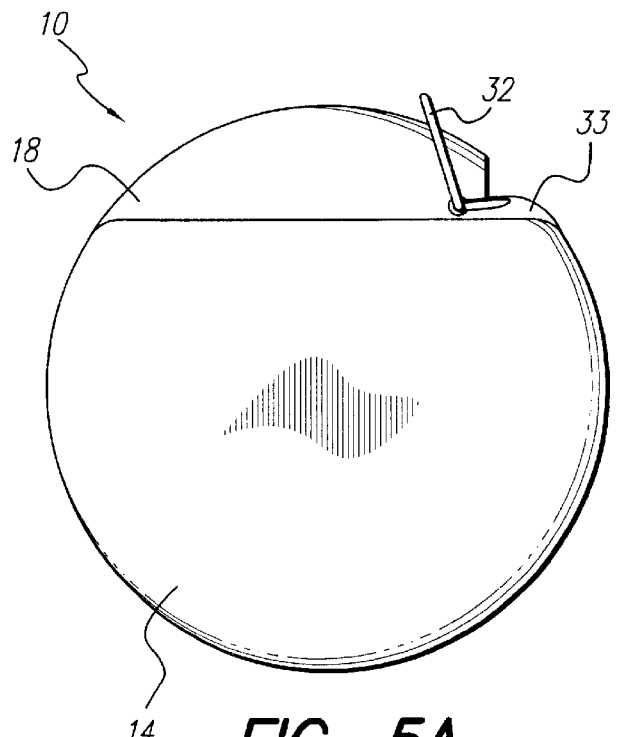
FIG. 5A is a front view of an alternative configuration of the clip lock mechanism of another embodiment of the present invention and medical device of the type that may be used with the present invention.

Furthermore, the clip may be attached to the header or device in various locations. One alternative configuration is seen in FIG. 5A. In this alternative configuration, the base of header 18 extends entirely across case 14, so that the underside of lead plug 28 contacts a shoulder portion 33 of the header when connector 22 is inserted into receptacles 20. In the previous embodiment, as shown in FIG. 3A, the header extends across case 14 only to a position flush with the openings to receptacles 20, and there is no shoulder portion. Thus, in the previous configuration, the underside of lead plug 28 directly contacts case 14.

Figure 5B:
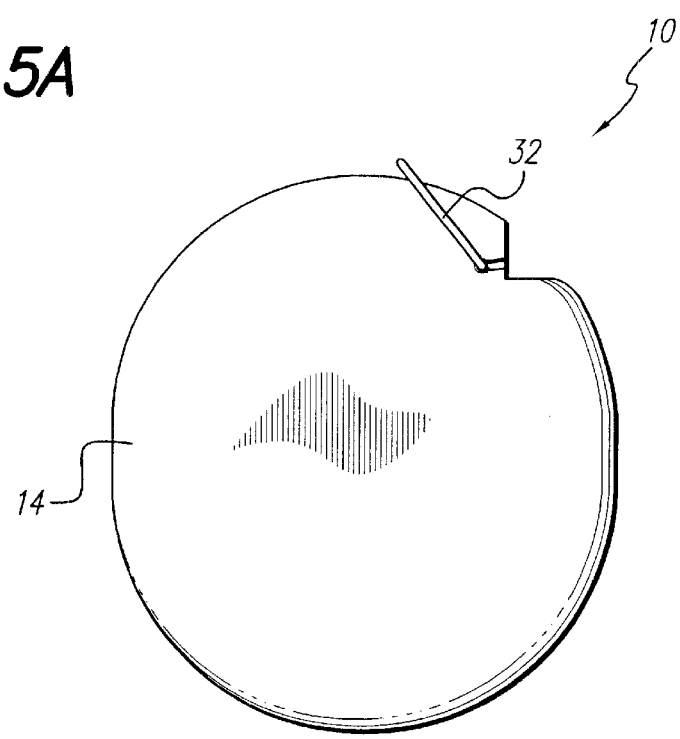
FIG. 5B is a front view of an additional alternative configuration of the clip lock mechanism of another embodiment of the present invention and medical device of the type that may be used with the present invention.

As mentioned earlier, the present invention also applies to use with a "headerless" device, as seen in FIG. 5B. In addition, the clip may be attached via means other than insertion into a hole or indentation. For instance, the clip may be attached to the device via a hinge type mechanism. Alternatively, the clip may be a two piece device comprising a rod attached to the device and a generally U-shaped piece of wire that pivotally connects to the ends of the rod.

Figure 6A:
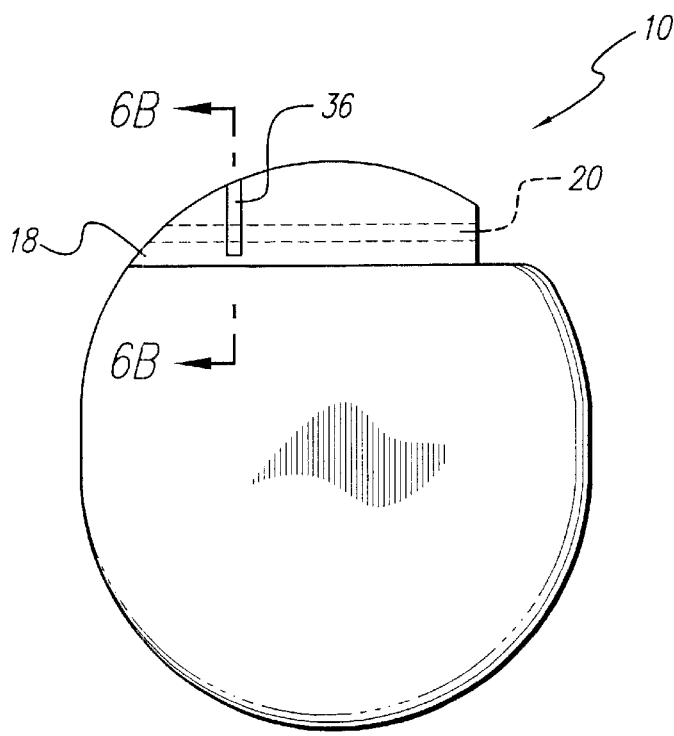
FIG. 6A is a front view of a clasp of another embodiment of the present invention, and medical device of the type that may be used with the present invention.
Figure 6B:
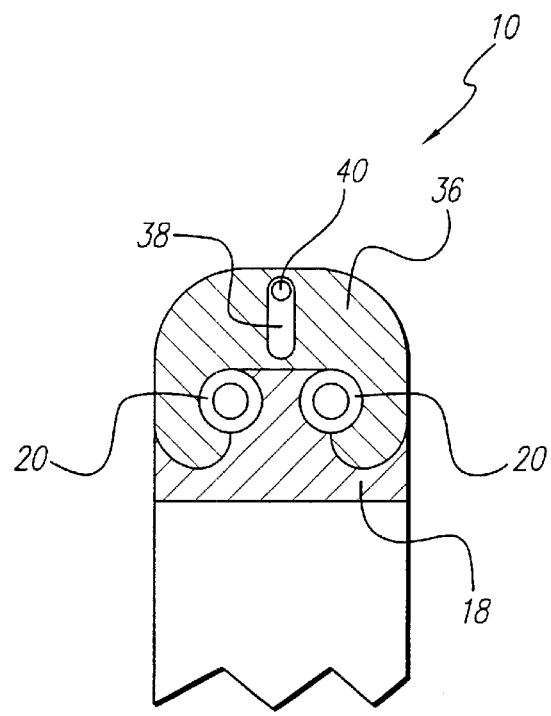
FIG. 6B is a side view of the clasp of FIG. 6A of another embodiment of the present invention, and medical device of the type that may be used with the present invention.

Alternative embodiments of the clip mechanism include a clasp 36 that secures to the lead pin once the pin is inserted in the lead receptacle 20 (FIGS. 6A and 6B). A slot provided in device 10 would allow clasp 36 to slide into place around the lead pin, which may be provided with indentations for increasing the reliability of the connection. Clasp 36 may include a clasp slot 38 and clasp pin 40 that allow the clasp to release the lead pin without the clasp separating from device 10.

Figure 7A:
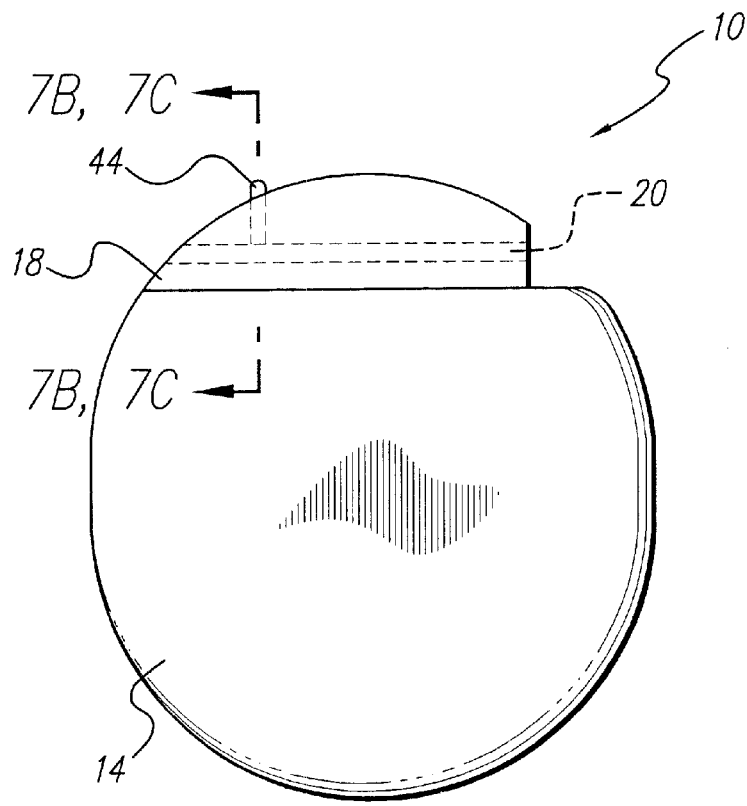
FIG. 7A is a front view of a cam mechanism of another embodiment of the present invention, and medical device of the type that may be used with the present invention.
Figures 7B, 7C:
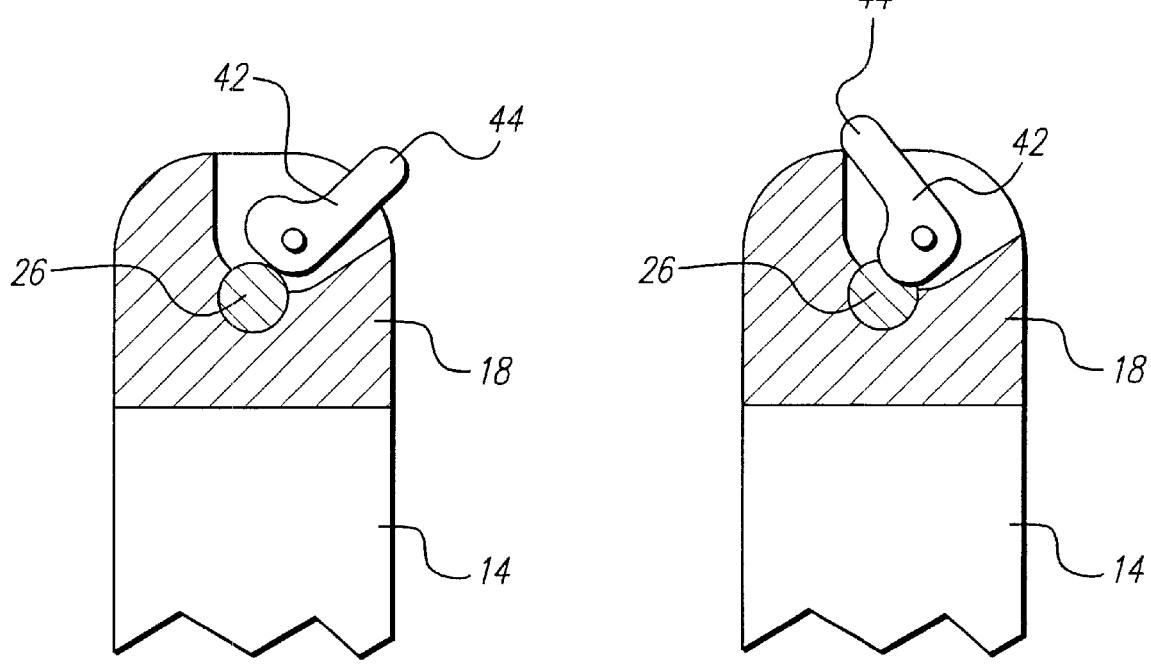
FIG. 7B is a side cross-sectional view of the cam mechanism taken along line 7B—7B of FIG. 7A of another embodiment of the present invention, with the cam mechanism in an unlocked position, and medical device of the type that may be used with the present invention.
FIG. 7C is a side cross-sectional view of the cam mechanism taken along line 7C—7C of FIG. 7A of another embodiment of the present invention, with the cam mechanism in a locked position, and medical device of the type that may be used with the present invention.

A further embodiment, shown in FIGS. 7A, 7B, and 7C, comprises a rotating cam mechanism 42 comprising a part of the device enclosure, located between the lead receptacle 20 and the outer surface of the enclosure, with a tab 44 for actuating the cam. As mentioned earlier and illustrated with this embodiment, the present invention relates not only to the use of multiple receptacles 20 for multiple lead pins 26, but also to the use of a single receptacle 20 for a single lead pin 26. As shown in FIG. 7B, before and during insertion of the lead pin 26 into the lead receptacle 20, the cam is in an unlocked position with tab 44 protruding from the enclosure. After the pin is in place within the receptacle, tab 44 is actuated (with a tool or preferably with a finger) into a locked position, as shown in FIG. 7C. The cam thus provides sufficient force to hold the pin securely within the receptacle. For increased reliability of the connection, the pin may have an indentation that fits a portion of the cam mechanism when the cam mechanism is in locked position.

In yet another embodiment, shown in FIGS. 8A, 8B, and 8C, a spring-loaded pin 48 comprises a part of the device enclosure, located between lead receptacle 20 and the outer surface of the enclosure. Spring-loaded pin 48 typically comprises a helical compression spring 50 biased into a position that causes the distal tip 52 of spring-loaded pin 48 to protrude into lead receptacle 20. During insertion into lead receptacle 20 (shown in FIG. 8B), lead pin 26 pushes the distal tip 52 of spring-loaded pin 48 in a proximal direction, which in turn compresses spring 50. Once lead pin 26 is fully inserted (shown in FIG. 8C), distal tip 52 is pushed distally by spring 50 into depression 54 in the side of lead pin 26. Depression 54 is located in lead pin 26 to be in alignment with spring-loaded pin 48 when lead pin 26 fully inserted, thus securing lead pin 26 in proper position within lead receptacle 20. Spring-loaded pin 48 is preferably fully contained within the device but may also have at its proximal end a head which protrudes through the outer surface of the enclosure, by which the attitude of spring 50, distal tip 52, and lead pin 26, may be determined. Suitable spring-loaded pins are commercially available from Interconnect Devices, Inc. of Kansas City, Kans.

As will be evident to one of ordinary skill in the art, the above clip lock 32, clasp 36, cam mechanism 42, spring-loaded pin 48, and similar mechanisms apply to connections other than between an implantable device and a lead or lead extension. For instance, other connections found between components of a typical implantable medical device are illustrated in the block diagram of FIG. 9. Some of these components are implanted and some are external. The implanted components may include implanted medical device 100 which interfaces with an electrode array(s) positioned on one or more implanted leads 110. This interface may occur through one or more implanted lead extensions 120. For testing and/or fitting purposes, the electrode array of implanted lead(s) 110 may also interface with an external trial device 140 through one or more percutaneous lead extensions 132. During implant surgery, external trial device 140 is typically connected to percutaneous lead extension(s) 132 through external cable(s) 134. Each interface between components is illustrated in FIG. 9 as a line with an arrow and, whether internal or external, may use clip lock 32, clasp 36, cam 42, spring-loaded pin 48, or similar mechanism to ensure a secure connection. Additional alternative means will be apparent to those skilled in the art from reading the specification and reviewing the drawings herein, without deviating from the spirit of the instant invention.

Thus, the invention provides a simple, yet reliable and easy-to-use approach for detachably securing an implantable device to an implantable lead, which lead has multiple contacts therein (which contacts respectively attach to electrodes or other devices or components at a distal end, or along the length of, the lead). The locking clip mechanism of the present invention also provides a secure and evident connection without the use of a tool, thus reducing surgery time, risk of infection, and likelihood of error. With the clip in place, the connection is reliable electrically and mechanically, so that it resists body fluids, flexing, and other forces, yet it is compact and light-weight.

While the invention herein disclosed has been described by means of specific embodiments and applications thereof, numerous modifications and variations could be made thereto by those skilled in the art without departing from the scope of the invention set forth in the claims. For example, the case may also be used to house or protect other types of assemblies, in addition to electronic circuit assemblies. For example, a housing may be used to protect an implantable hydraulic assembly, or an implantable electromechanical pump (e.g., an insulin pump), in which certain components need to be protected from the environment within the human or other body. Such assemblies may communicate with external components via a header assembly and lead system as described above which has hermetic feed-through posts, e.g., hermetic pipettes for communicating a fluid to an electromechanical pump and/or hermetic electrical feedthrough terminals and connectors for making electrical connection with electronic circuitry.

What is claimed is:

1. An implantable medical device comprising components housed within an enclosure, wherein the components are configured to carry out a desired function, the medical device further comprising:

at least one lead, the at least one lead terminating in a lead connector;

at least one receptacle within the enclosure for receiving at least one lead connector comprising at least one lead pin; and a clip pivotally mounted to the enclosure;

wherein the at least one lead pin of the at least one lead connector is inserted into the at least one receptacle; and wherein the clip pivots over the at least one lead connector to secure the at least one lead to the enclosure.

2. The implantable medical device of claim 1 wherein the clip is configured for manipulation with a finger to lock the lead to or unlock the lead from the enclosure.

3. The implantable medical device of claim 2 wherein the clip comprises a metal alloy wire bent into a generally rectangular shape with the ends of the wire inserted into the enclosure.

4. The implantable medical device of claim 3 wherein the metal alloy comprises nitinol.

5. The implantable medical device of claim 3 wherein the ends of the wire are welded together.

6. The implantable medical device of claim 1 wherein the lead connector comprises a lead plug configured with grooves or indentations for receiving the clip.

7. The implantable medical device of claim 1 wherein the enclosure further comprises:

a case; and a header hermetically attached to the case;

wherein the clip is pivotally mounted the header; and wherein the at least one receptacle is located in the header.

8. The implantable medical device of claim 7 wherein the clip is configured for manipulation with a finger to lock the lead to or unlock the lead from the enclosure.

9. The implantable medical device of claim 7 wherein the lead connector comprises a lead plug configured with grooves or indentations for receiving the clip.

10. The implantable medical device of claim 7 wherein the case is made from titanium.

11. The implantable medical device of claim 7 wherein the case is made from ceramic material.

12. An implantable medical device comprising:

(a) a ceramic or titanium case;

(b) device components mounted within the case;

(c) a header molded to the case;

(d) at least one receptacle formed within the header for receiving at least one lead connector;

(e) feed through terminals extending from the components within the case to the at least one receptacle within the header; and (f) a lead system including at least one lead connector at the proximal end of a lead or lead extension, wherein the at least one lead connector comprises at least one lead pin and at least one lead plug;

wherein the at least one lead pin is inserted into the at least one receptacle, thereby making contact with the components within the case through the feed through terminals; and (g) a clip pivotally mounted to the header;

wherein the clip is pivoted into place against the at least one lead connector, thereby securely locking the lead connector to the device.

13. The implantable medical device of claim 12 wherein the clip is configured for manipulation with a finger to lock the lead connector to or unlock the lead connector from the from the device.

14. The implantable medical device of claim 12 wherein the lead connector comprises a lead plug configured with grooves or indentations for receiving the clip.

15. A method of securing at least one lead to an enclosure of an implantable medical device, comprising:

(a) providing a lead connector at the proximal end of the at least one lead, the lead connector comprising at least one lead pin and at least one lead plug;

(b) providing in the enclosure at least one receptacle for receiving at least one (c) pivotally mounting a clip to the enclosure;

(d) inserting at least one lead connector into the at least one receptacle; and (e) pivoting the clip into place over the at least one lead plug to secure the at lead least one lead to the enclosure.

16. The method of claim 15 wherein pivoting the clip into place over the lead plug comprises using a finger to pivot the clip to lock and unlock the lead and enclosure.

17. The method of claim 15 wherein the lead plug is configured with grooves or indentations for receiving the clip.

18. The method of claim 15 wherein the clip consists essentially of nitinol.

19. The method of claim 15 wherein the enclosure is formed of a hermetically sealed case and header, the clip is mounted to the header, and the at least one receptacle is provided in the header.

20. The method of claim 19 wherein the header consists essentially of epoxy.

21. The method of claim 19 wherein the case consists essentially of titanium.

* * * * *